United States Patent [19]

Wegmann

[11] 4,340,531

[45] Jul. 20, 1982

[54] AQUEOUS-MEDIA DISPERSIBLE, HIGHLY-CONCENTRATED, FINELY-DISPERSE, LOW-DISPERSANT OR FREE-OF-DISPERSANT PREPARATION OF HARDLY WATER-SOLUBLE TO WATER-INSOLUBLE ACTIVE SUBSTANCES IN SOLID FORM, PROCESS FOR THEIR PREPARATION AND THEIR APPLICATION

[75] Inventor: Jacques Wegmann, Bettingen, Switzerland

[73] Assignee: Rohner AG Pratteln, Pratteln, Switzerland

[21] Appl. No.: 117,800

[22] Filed: Feb. 1, 1980

[30] Foreign Application Priority Data

Feb. 2, 1979 [CH] Switzerland ................... 1057/79

[51] Int. Cl.$^3$ .............................................. C08K 5/00
[52] U.S. Cl. ................................. 524/556; 524/549; 524/81; 524/86; 524/88; 524/190
[58] Field of Search ............... 260/42.21, 42.43, 42.57, 260/32.6 R, 33.2 R, 33.4 R, 42.49, 42.52; 8/594, 597

[56] References Cited

U.S. PATENT DOCUMENTS

| | | | |
|---|---|---|---|
| 3,385,808 | 5/1968 | Bonin et al. ...................... | 260/42.21 |
| 3,440,192 | 4/1969 | Hoy et al. ....................... | 260/33.2 R |
| 3,856,725 | 12/1974 | Montesissa et al. ............. | 260/32.6 R |
| 3,873,495 | 3/1975 | Appel et al. ..................... | 260/42.52 |
| 3,970,633 | 7/1976 | Miller et al. .................... | 260/42.52 |
| 3,978,016 | 8/1976 | Perronin et al. ................. | 260/42.21 |
| 4,125,499 | 11/1978 | Howard .......................... | 260/32.6 R |
| 4,198,333 | 4/1980 | Bonin et al. ...................... | 260/42.57 |
| 4,202,815 | 5/1980 | Wegmann ........................ | 260/42.21 |
| 4,244,863 | 1/1981 | Hemmerich et al. ............. | 260/42.52 |

FOREIGN PATENT DOCUMENTS

| | | |
|---|---|---|
| 1108212 | 4/1968 | United Kingdom . |
| 1176217 | 1/1970 | United Kingdom . |
| 1311185 | 3/1973 | United Kingdom . |
| 1474112 | 5/1977 | United Kingdom . |
| 1491736 | 11/1977 | United Kingdom . |
| 2001091 | 1/1979 | United Kingdom ............. 260/42.57 |
| 1550095 | 8/1979 | United Kingdom . |

*Primary Examiner*—Lewis T. Jacobs

[57] ABSTRACT

Highly concentrated, finely dispersed, dispersant-poor or dispersant-free preparation of active substances in solid form hardly soluble to insoluble in water, dispersible in aqueous media, process for making these preparations and applications of same.

The preparation contains:

(a) 40 to 90% by weight of at least one active substance hardly soluble or insoluble in water with a mean particle size less than 5 microns, (b) 10 to 60% by weight of at least one water-soluble salt of an acid resin, and (c) 0 to 50% by weight of further additions such as dispersants, wetting agents or diluents or a mixture of these.

The preparation is finely disperse and in the form of a powder or granulate.

The preparation can be made as follows:

(a) a mixture of active substance(s) and water-insoluble acid resin is treated with a solution of alkalies or amines in water or solvents and the liquid then is removed.

(b) a mixture of active substance(s) and water-insoluble acid resin is exposed to the vapors of ammonia or volatile amines.

(c) a mixture of active substance finely dispersed in water and an aqueous solution of the acid resin salt is subjected to spray drying.

The preparation can be used as an aqueous or aqueous-organic dispersion.

7 Claims, No Drawings

AQUEOUS-MEDIA DISPERSIBLE, HIGHLY-CONCENTRATED, FINELY-DISPERSE, LOW-DISPERSANT OR FREE-OF-DISPERSANT PREPARATION OF HARDLY WATER-SOLUBLE TO WATER-INSOLUBLE ACTIVE SUBSTANCES IN SOLID FORM, PROCESS FOR THEIR PREPARATION AND THEIR APPLICATION

The present invention relates (1) to highly concentrated, finely disperse preparations in solid form as powders or granulates, which preparations are easily and completely dispersed in aqueous media and contain few or no dispersants, said preparations being of active substances which are hardly soluble in water or not at all; (2) to processes for making these preparations; (3) to the application of these preparations for producing dispersions of the active substance in aqueous or aqueous-organic media; and (4) to the application of the dispersions in manners known per se. Pertinent active substances are, for instance, insecticides, herbicides, pharmaceuticals, textile auxiliary products, textile finishing means, and plastic additives, especially, however, natural or synthetic dyestuffs or their intermediate products, optical brighteners and pigments.

The preparations of the invention can be dispersed in aqueous media without employing special methods or additives, by merely stirring, it thus being possible to obtain finely disperse and stable, diluted or concentrated dispersions of the active substances.

Solid preparations of dyestuffs or pigments and acid resins insoluble in water are known. For instance, such dispersions which are easily dispersed in organic media are described in German Offenlegungsschrift No. 26 06 212 and German Auslegeschrift No. 1 469 724 (corresponding to British Pat. No. 1,108,076), while Swiss Pat. No. 533 669 describes those preparations which can be dispersed both in aqueous and in organic media. The latter preparation contain styrene maleinate copolymers as the carrier material; they can be dispersed in aqueous media only by stirring with addition of alkalies. According to the examples of implementation, finely distributed dispersions were obtained after shaking for one hour.

German Offenlegungsschrift No. 28 17 453 (and corresponding U.S. application Ser. No. 888,417 U.S. Pat. No. 4,202,815, issued May 13, 1980 describes a process for making preparations dispersible in aqueous media and consisting of powders or granulates, which contain as carrier substances high-molecular organic compounds from slightly soluble to insoluble in water, containing acid groups and convertible into a water-soluble form by means of bases, said dispersions being more rapidly and more easily dispersed than the above-mentioned preparation. These preparations also suffer from the fundamental drawback that they require being dispersed in an excess of a relatively concentrated alkali solution, which may be troublesome depending on the application of the dispersion. However, a subsequent neutralization of the present excess alkali is not a simple matter and may degrade the quality of the dispersion; therefore such a step is viewed as an undesirable complication restricting the range of applicability of the preparations.

The preparations of the invention do not suffer from the above-cited drawbacks, and additionally offer other advantages to those of the known preparations.

Again, solid, reversibly dispersing preparations of active substances free of dispersants and merely containing a water soluble, high-molecular carrier substance, already have been proposed. "Reversibly dispersible" means that the dispersions obtained by stirring a solid preparation into a liquid medium have the same degree of fineness as the dispersion from which the preparation was made. British Pat. No. 1,176,217 describes preparations of this type containing cellulose derivatives carrier material. These carrier substances may be soluble either in aqueous or in organic media. The dispersibility of the preparations in aqueous or organic media depends on the solubilities of the carrier substances. Aqueous-media dispersible preparations containing water-soluble cellulose-based carrier substances have failed to find industrial acceptance. Presumably this is because redispersible preparations must contain relatively large amounts of carrier substance which swells only slowly in water, whereby the preparations will only dissolve after substantially length stirring (for instance of one hour).

On the other hand, the known preparations based on water-soluble, low-molecular dispersants such as lignin sulfonate or condensation products of naphthalene sulfonic acid with formaldehyde can be quickly and completely dispersed by merely being stirred in water. However, they suffer from a set of other shortcomings. In particular the waste water is loaded by the contents found in such preparations of partly strongly foaming dispersants. Furthermore, these dispersants affect undesirably various applications of these preparations. In the textile application of dyestuffs, whether it be by dyeing or by printing, they exert for instance a troublesome retention effect and favor the undesired dyestuff migration during the drying of the textiles, that is, they keep the dye either in the dyeing bath, or, in pad dyeing, on the surface of the textiles, they make difficult the rinsing of non-fixed dye and cause coloration of the white spaces in prints when used in conventional amounts. As long as the dispersants remain in the substrate to be treated, which is most of all the case for bulk applications (for instance spin dyeing), they may furthermore affect the fastness of the dyeing or result in yellowing the substrate. When using plant protective means, the dispersants cause the formation of water-susceptible coatings, which are easily rinsed off the treated plants, will poorly adhere to them, and therefore represent coatings of little effectiveness.

The preparations of the invention are free from the cited drawbacks, without thereby incurring others as a trade-off. Where the preparations are meant for pharmaceutical purposes, they furthermore offer the advantage that carrier substances can be used which are known to be physiologically unobjectionable and which already are being used for coating tablets with a protective layer or for the printing of food wraps.

It has already been proposed to make preparations which are free both of carrier substances and dispersants and containing only the active substance, for instance by wet granulation in a poly-phase system; preparations are to be so obtained which allow easy and complete dispersion both in aqueous and organic media. Preparation of this type are described for instance in German Offenlegungsschrift No. 24 59 457 (corresponding to British Pat. No. 1,491,736). To the extent these substances contain water-insoluble active substances, the above data, however, could not be corroborated.

Therefore it was surprising that without special steps or additions, preparations could be obtained which are easily and completely dispersed in water and contain little or no dispersant, provided that water-soluble salts of acid resins be used as the carrier substances.

The preparations of the invention contains:

(a) 40 to 90% by weight, preferably 50 to 80% by weight of at least one active substance which is from slightly soluble to insoluble in water and has a mean particle size less than 5 microns, preferably less than 2 microns, (b) 10 to 60% by weight, preferably 20 to 50% by weight of at least one water-soluble salt of an acid resin, preferably a maleinate resin, a maleic-acid copolymer or a polymer or copolymer of a maleic-acid derivative, and (c) 0 to 50% by weight of further additives such as dispersants, wetting agents, fillers or diluting agents or their mixtures.

These preparations therefore contain physiologically and ecologically unobjectionable carrier substances and are suited for applications in aqueous media in the most finely dispersed form. They may contain active substances which are from slightly soluble to insoluble in water and are obtained from an entire series of classes of compounds to be applied in this matter; examples of such active substances are insecticides, herbicides, flame retardants, antioxidants, stabilizers, cosmetics and pharmaceuticals, but in particular such natural dyestuffs as carotinoids, synthetic dyestuffs or dyestuff-forming agents such as deprotonized basic dyestuffs, mordant dyestuffs, solvent dyestuffs, metallic-complex dyestuffs, disperse dyes, naphthol dyes and vat dyes, inorganic pigments such as lampblack, titanium dioxide, iron oxide hydrates, various metal powders, chromium oxide and ultramarine, or organic pigments such as those of the azo, anthra, quinone, phthalocyanine, nitro, perinone, perylenetetracarboxylicacid diimide, dioxazine, indolinone, imidazole, quinacridone, indigo and thioindigo series. Applicable disperse dyes especially are also the reactive disperse dyes, and as regards Thermotransfer printing, for minimal deposition processes (deposition without excess liquor which would have to be removed) or for rinsing with very little water or solvents, specific disperse dyes are applicable, as the preparations of the invention are especially well suited for these new processes. The preparations also may contain various active substances, for instance water-insoluble textile finishing means together with dyestuffs or pigments or dyestuffs of various classes, such as vat dyes together with disperse dyes, or dyestuffs with pigments.

Suitable acid resins, of which the water-soluble salts are used as carrier substances of the invention, are in particular water-insoluble acid resins which can be easily converted into water-soluble salts through the effects of gaseous bases. Very generally those natural and synthetic acid resins are applicable as are described in KARSTENS LACKROHSTOFFTABELLEN, 4th ed., 1967 through 6th ed. 1976, Curt R. Vincentz publisher, Hanover (West Germany). Preferably, the water-soluble salts are selected from the group consisting of salts of maleinate resins, salts of polymers containing monomeric maleic acid, and salts of polymers containing monomeric maleic acid derivatives. Particularly well suited are reaction products of acid resins with maleic acid and polyalcohols (for instance pentaerythrite), further copolymers of maleic acid containing free acid groups or their derivatives (such as maleic acid anhydride or maleic acid half-esters) which olefins (such as ethylene, propylene or butylene) or other unsaturated compounds (such as vinylethers, vinylesters, vinyl chloride and styrene). Partly esterified copolymers of maleic acid with styrene are especially applicable.

The acid resins should be high-molecular, that is, their molecular weights should exceed 500, preferably 1,000. Molecular weights exceeding 100,000 however are less suitable as a rule because when using water-soluble salts of acid resins with molecular weights so high, preparations would result that are more difficult and slow to disperse in aqueous media and of which the dispersion would exhibit too high a viscosity. The best results are obtained with mixtures of water-soluble salts of acid resins of various molecular weights, because water-soluble salts of acid resins with molecular weights from 1,000 to 2,000 show the best effects as components in ground form, whereas water-soluble salts of acid resins with molecular weights of 20,000 to 50,000 offer the best results regarding completely reversible dispersibility.

The alkali metal salts, ammonium salts and preferably the amine salts, such as the salts with aliphatic, alicyclic or aromatic amines may be used as the water-soluble salts of acid resins. Especially suitable for the production of such salts are ammonia and highly volatile amines such as ethylamine, diethylamine, trimethylamine and triethylamine.

The preparations of the invention contain at least 10% by weight of the carrier substance (component b), in order that they be satisfactorily reversibly dispersible. Proportions exceeding 60% in carrier substance offer no advantages. Where preparations with a low proportion in active substance (component a) are required, up to 50% by weight of inert, water-soluble standardizing agents (component c) may also be added in addition to the carrier substance in lieu of high proportions of latter.

The preparations may contain quite generally further additions up to 50% by weight. Examples of such additions are the above-cited, water-soluble standardizing agents, further other diluting agents, binders, wetting agents and dispersants. Water-insoluble additions such as chalk dust, aluminum oxide hydrate or teflon powder should possess at least the same degree of fineness (at most the same average particle size) as the active substance. Examples of water-soluble diluents (standardizing agents) are water-soluble amides, hydroxyl- and ether-compounds such as sorbite or urea, and natural or synthetic polymers such as alginates, polyamides or polymethacrylates. If the carrier substance(s) (component b) shoud lack a wetting effect, wetting agents may be advantageously added, so that powdery preparations in water be rapidly wetted. If the preparations are obtained by spray-drying, they may contain where appropriate dispersants and/or wetting agents used in the grinding of the active substance, for instance polyvinylpyrrolidone and other non-ionic dispersants such as fatty-alcohol/ethylene-oxide condensation products. For instance, the preparations may contain up to 10% by weight of anionic and/or non-ionic dispersants. When grinding the active substance, however, use may also be made of water-soluble salts of low-polymeric maleinate resins or styrene-maleinate-copolymers. In this case the preparations contain no dispersants at all.

The preparations of the invention may be obtained by converting an aqueous dispersion of the finely comminuted active substance (component a) in the presence of a dissolved water-soluble salt of an acid resin (component b), possibly in the presence of dispersants and/or diluents (component c) by means of gentle or rapid drying (for instance by freeze-drying or especially by spray drying) into a solid preparation, that is, a powder or a granulate.

Such a procedure may be as follows: the active substance is comminuted in an aqueous medium in the presence of small amounts of a dissolved water-soluble salt of an acid resin or a dissolved water-soluble dispersant until the required mean particle size is obtained, for instance in a ball-mill agitator. Following separation of the ground substance, the carrier substance is added in an amount sufficient to obtain a reversibly dispersing preparation, and the preparation is dried. As the dispersion is quite thermally stable, fluidized-bed drying or especially spray-drying at high temperatures may be used, which are especially economical.

A further and especially advantageous process which can surprisingly be applied to obtain the preparations of the invention consists in first making in a manner known per se a solid preparation from the active substance and the required amount of water-insoluble acid resin and then in converting the acid resin contained in the solid preparation by subjecting it to gaseous ammonia or to the vapor of a volatile amine into a water-soluble salt. Surprisingly this is possible even for dried, powdery or ganulated preparations. The salt formation, however, will take place somewhat more rapidly if the preparation, for instance due to the production, still contains water or solvents. If the salt formation is carried out by gassing on a suction filter after the separation from a liquid, it is, however, necessary for the preparation to be in loose, granular form rather than as, say, a compact filter cake which cannot be crossed by the vase's vapors.

The preparations of active substances and water-insoluble acid resin serving as raw materials for the gassing by a base can be carried out by the known processes for obtaining such preparations. For instance the solvent/salt-kneading method may be used which is described in Swiss Pat. No. 533 669 and discussed therein at length. However, the less costly and more efficient two-phase process may be used, which is described in German Offenlegungsschrift 28 17 453 and the corresponding U.S. application Ser. No. 888,417, U.S. Pat. No. 4,202,815, issued May 13, 1980. With respect to using kneaders, this process holds the further advantage that the acid resin is subjected to no mechanical stresses and therefore reliably will escape damage and that the comminution of the active substance can be carried out to the desired average particle size in aqueous and organic media. The selection of the comminution medium depends only on which variation is the more advantageous. This depends on the type of the active substance and can be easily ascertained by preliminary tests.

The preparations so obtained and consisting of active substance and water-insoluble acid resin obviously can also be converted by means of solutions of alkalies, ammonia or amines in water or solvents and then removal of the liquid into preparations containing a water-soluble salt of the acid resin.

The later conversion of the acid resin into a water-soluble salt is more universal than the process starting from an already water-soluble salt because the active substance can be comminuted not only in an aqueous, but also in an organic medium to the desired mean particle size and because the combination of the finely comminuted active substance with the water-insoluble acid resin and the ensuing conversion of the acid resin into a water-soluble salt can be carried out at low temperatures without supplying heat. These factors are most of all significant for those active substances which cannot be ground in an aqueous medium because they either would decompose or be transformed into a modified form, and for active substances which are sensitive to heat and cannot be exposed to higher temperatures even for a short time.

Depending on the production method, the preparations of the invention range from fine-powder to granular in size. Granulates as a rule offer the advantage that they flow freely, generate little dust and are friable.

It suffices, to transform the preparations into dispersions, to pour water over them or stir them into water, as a rule. In this manner one obtains already after a short while finely dispersed, homogeneous dispersions free from undispersed or undissolved residues. Depending on the application, these dispersions, dilute or concentrated, may receive further additions such as thickeners or dispersants. An addition of dispersants for instance will be required where the dispersions are exposed to especially harsh conditions, such as occur when dyeing under pressure at high temperatures. When the dispersions are applied in spin-dyeing of viscose fibers, it will again be advantageous to add anionic dispersants such as dinaphthylmethane disulfonates, to ensure the stability of the dispersion in contact with the reducing, soda-alkaline cellulose xanthogenate solution (viscose). In most cases however, the preparations obtained can be applied directly with additional means or steps.

The numerous applications for the dispersions of the invention, which are known per se, already were comprehensively described with respect to the state of the art and therefore further data is not required here.

The invention is described in further detail below, without thereby being restricted to such illustrations. Parts are by weight, and the temperatures are in °C.

EXAMPLE 1

40 parts of a raw dyestuff obtained by diazotizing a mixture of o- and p- ethylaniline and coupling the mixture so achieved of diazonium compounds with 3-hydroxy-2-naphthoicacid-2',5'-dimethoxyanilide, are ground in the presence of 1 part of polyvinyl pyrrolidone and 1 part of dinaphthylmethane disulfonate in a ball-mill agitator with 300 parts of glass balls 1 mm in diameter in 58 parts of water until the mean particle size of the dyestuff is less than 2 microns. After separating the dispersion from the glass balls, it is thoroughly mixed by stirring or agitation with a solution of 10 parts of a styrene-maleinate resin with an average molecular weight of 40,000 in 80 parts of aqueous methylethyl ketone and thereupon it is gradually diluted with water until the preparation separates in the form of a granulate. Then the aqueous phase containing the solvents is evacuated by suction, the preparation is washed with water and dried. The granulate so obtained is stored in an atmosphere of ammonia vapors until no further weight increase can be observed, and until a sample of the granulate is easily and completely dispersed at room temperature in water and no residue can be ascertained when filtering the dispersion through a filter paper.

If the ammonia vapors are replaced by those of ethylamine, diethylamine or triethylamine, or if the gassing is carried out before drying the granulate, and drying takes place only thereafter, similarly good preparations are obtained.

If the said styrene maleinate is replaced in part or in whole by a styrene-maleinate resin with an average molecular weight of 2,500, then also well-dispersing preparations are obtained, of which the concentrated aqueous dispersion is of a lesser viscosity.

The aqueous dispersions are suited—following addition of dispersants or thickeners—for the dyeing or printing of snythetic fibers by processes known per se. As regards impregnation processes, the aqueous dispersion however may also be used without additives; this facilitates aftertreatment operations such as after-washing when using minute amounts of water or solvents.

EXAMPLE 2

40 parts of the azo dye obtained by coupling diazotized nitrotoluidine with methylpyrazolone are ground in the presence of 1 part of the morpholine salt of a styrene maleinate resin with a molecular weight of 2500 and an acid number of 175 in a ball-mill agitator while using 300 parts of zirconium oxide balls about 2 mm in diameter in 59 parts of water until the average particle size of the azo dye is less than 2 microns. After removing the balls, 9 parts of sorbite and 10 parts of a styrene maleinate resin with a statistical molecular weight exceeding 40,000 and present half as amide, half as ammonia salt, are added to the dispersion. The resulting dispersion then is diluted with 20 parts of water and spray-dried at a gas entry temperature of 120° C. A preparation in the form of a loose powder and easily dispersed in aqueous media is thus obtained.

If in lieu of the above-cited dyestuff one of the others in example 2 of the British Pat. Nos. 1,221,126 cited disperse dyes is used, and if the procedure otherwise is the same as above, then similarly good preparations are obtained, which are especially well suited for sublimation transfer printing based on aqueous or aqueous-organic printing inks.

Similarly good preparations are obtained using the conditions of examples 1 or 2 when utilizing reactive disperse dyes, for instance with that dye obtained by diazotizing chloroacetyl-p-phenylenediamine and coupling on p-cresol, or with 1,4-di-(chlorohydrinamino)-anthraquinone (C.I. Reactive Blue 6).

Methyl cellulose, polyglycolethers or urea can also be used as diluents instead of sorbite.

EXAMPLE 3

50 parts of 1-anilino-3,5-(1-anthraquinonyl-amino)-triazine are ground in the presence of 1 part of dinaphthylmethan disulfonate in a ball-mill agitator while using 300 parts of glass balls of 1 mm diameter in 49 parts of water until no particles exceeding 1 microns remain in the dispersion. The dispersion separated from the glass balls is filtered and then mixed with a solution of 12.5 parts of a styrene-maleinate resin with a mean molecular weight of 40 000 in 80 parts of methylethyl ketone. This is followed by diluting with water until a well-filtrable, granular precipitate is obtained, by washing with water and drying. The granulate is exposed to an ammonia atmosphere until a sample can be easily and completely dispersed in water. When the dyestuff content in the preparation is raised to 90% by weight, a preparation which can still be well dispersed is obtained, and with a low viscosity.

If the above vat dye is replaced by other raw vat dyes such as dichloroindanthrone, pyranthrone, flavanthrone, 1,5-dibenzoylaminoanthroquinone and possibly halogenated anthranthrone or dibenzylpyrenequinone, and if the procedure otherwise is as described, similarly good preparations will be obtained.

The preparations are easily and wholly suitable for vats and can be applied to cellulose fibers by conventional methods. As regards mixed fabrics, they may be applied jointly with preparations per examples 1 or 2 from dispersion dyestuffs. When dyeing cotton-polyester fabrics by the pad process, they result in a uniform article appearance and evidence less of migration than conventional commercial powder preparations.

In in lieu of the methylethyl ketone, use is made of an identical amount of pentoxon (4-methoxy-4-methylpentanon-2), methylacetoacetate, ethylacetoacetate or propylene carbonate or mixtures of these, and if the procedure otherwise is the same, good preparations again will be obtained.

If one third of the above said dyestuff is replaced by Colour Index Disperse Yellow 99, a well dispersing preparation also is obtained, which results in stable, aqueous dispersions.

EXAMPLE 4

30 parts of lampblack are ground in the presence of part of dinaphthyl-methanedisulfonate in a ball-mill agitator with 300 parts of glass balls of 2 mm diameter in 69 parts of water until the average particle size of the lampblack is less than 1 micron. After removing the glass balls, 10 parts of a styrene-maleninate resin with a statistical molecular weight of 40,000 and present half as amide and half as ammonium salt are stirred into the dispersion, whereupon the preparation is isolated by spray drying with a gas entry temperature of 120° C. A loose powder dispersing well in aqueous media is obtained.

If in lieu of lampblack another pigment is used, for instance titanium dioxide, iron oxide, pigment brown 22 (Colour Index) or halogenated indanthron, and if the procedure otherwise remains the same, good preparations again will be obtained.

If the dinaphthylmethane-disulfonate is replaced by an equal amount of polyvinylpyrrolidone or by the ammonium salt of a maleinate resin with a molecular weight of 1000, then following the above conditions results in similarly good preparations.

The preparations can be used for pigment printing or for the spin dyeing of bulk materials.

EXAMPLE 5

40 parts of 2-hydroxyanthracene-3-carboxylic-acid-o-toluidide are mixed with 10 part of maleinate resin formed by condensing abietic acid with maleic acid and pentaerythrite, then are wetted with alcohol and dissolved in an aqueous sodium hydroxide solution. Thereupon the solution is acidified, the precipitate forming is filtered off, washed, dried and treated in an atmosphere of ammonia vapors until a constant weight is obtained. The resulting preparation is easily dispersed in an aqueous medium and can be rapidly and completely dissolved, upon addition of alkali hydroxides, with alcohol.

If the above components are used to make a preparation as described in the German Offenlegungsschrift No. 28 17 453 (U.S. application Ser. No. 888,417), and if it is thereupon treated with ammonia vapors, there results a friable ganulate with similarly good dispersing properties.

EXAMPLE 6

200 parts of an aqueous pressed cake of 5-nitro-2-amino-1-methoxybenezene (active substance=% by weight) are mixed with 2 parts of polyvinylpyrrolidone of a molecular weight of 40,000 and the mixture is set by means of water to an active substance content of 40% by weight. Then the mixture is ground in a ball-mill agitator until the mean particle size is about b 1-2 microns. After removing the glass balls, 20 parts of the ammonium salt of a styrene maleinate resin with an average molecular weight of 10,000 are stirred into the mixture and the preparation is subsequently isolated by spray drying at a gas entry temperature of 140° C. A loose, yellow powder is obtained, which can be easily dispersed in alkaline or also in neutral aqueous media. The dispersions can be very rapidly diazotized in complete manner at room temperature. Together with naphthol preparations of the type cited in example 5, but also together with untreated coupling components, the preparation can be used in very advantageous manner in the production of azo dyes in bulk or for dyeing or printing textile substrates.

EXAMPLE 7

20 parts of an optical brightener insoluble in water and cited in example 5 of the German Offenlengungsschrift No. 2 412 369 (British Pat. No. 1,474,112) are ground in the presence of 1 part of the ammonium salt of a maleinate resin until the average particle size of the brightener is less than 1 micron. After removing the glass balls, the dispersion obtained is mixed with 9 parts of the ammonium salt of a styrene maleinate resin with a molecular weight of 40,000 and the preparation is spray-dried (exhaust gas temperature: 80° C.). Preparations are obtained which in aqueous media form stable, easily distributed dispersions, whereas the granulated preparations obtained according to the illustrative implementation of the said German Offenlegungsschrift (or British patent) of the optical brighteners—in contrast with the corresponding preparations of the also cited water-soluble brighteners and in contrast with the statements made in said German Offenlegungsschrift or British patent—are not soluble in aqueous media and cannot be dispersed in them.

EXAMPLE 8

20 parts of 3-(p-chloroanilino)-10-(p-chlorophenyl)-2,10-dihydro-2-(isopropylimino)-phenazine (Clofazimin) are ground in the presence of 1 part of the ammonium salt of a maleinate resin in 60 parts of water until the particle size of the Clofazimin is less than 1 micron. After separating the grinding accessory, 4 parts of the ammonium salt of a styrene maleinate resin with a molecular weight of 40,000 are stirred in and the preparation is isolated following filtration through a 5 micron Kuno filter cartridge by spray drying. The resulting preparation is rapidly and easily dispersed in water. The dispersions depending on need can be thickened with water-soluble thickeners such as alginates or methylcellulose. They are used in skin treatment for leprous disease.

If the maleinate resin salt used in the grinding is replaced by an equal amount of polyvinylpyrrolidone and if the procedure otherwise remains the same as above, the result will be similarly good preparation.

If the above cited active substance is replaced by an equal amount of 2,2-dihydroxy-5,5-dichlorodiphenylmethane (Panacid) and if the procedure otherwise remains the same as above, a preparation easily dispersing in aqueous media is obtained which can be used for protection against moths and rotting by bacteria.

If a thiourea derivative is used as the active substance, as described in French Pat. No. 1 511 325, then preparations will result which can be dispersed in the finest form in water and in that form can be used against mollusks such as water snails.

When treated as described above, a triazine derivative prepared per U.S. Pat. No. 3,347,657 results in a herbicide preparation which disperses well in aqueous media and which adheres especially well on the substrate and is water-proof.

EXAMPLE 9

40 parts of pyranthron are vatted with addition of soda liquor and sodium dithionite in 1,000 parts of water. Then 10 parts of the ammonium salt of a styrene maleinate resin with an average molecular weight of 50,000 are stirred in. Next air is made to pass through the solution which thereafter is slightly acidified. The precipitate obtained is filtered off and washed. 50 parts of sodium lignin sulfonate are admixed before or after drying, the mixture is exposed to an atmosphere of ammonia vapors and where appropriate dried to completion. An easily vatting powder which disperses well is obtained.

If the lignin sulfonate is replaced by an equal amount of urea or sorbite or a mixture of these diluents, similarly good materials will be obtained.

If in lieu of the pyranthron another vat dye is used and if the procedure otherwise remains the same as above, again easily vatting preparations will be obtained.

If 40 parts of pyranthron are ground with 10 parts of the maleinate resin salt in a ball mill until the mean particle size of the pyranthron is less than 1 micron, and if 50 parts of diluent are added then and the product is isolated by spray drying, again a well-vatting preparation will be obtained.

I claim:

1. A process for making a preparation of active substances, hardly soluble or insoluble in water and in the form of powders or granules, said preparation being dispersible in an aqueous media, comprising:
   (a) 40 to 90% by weight of at least one active substance only slightly soluble or insoluble in water with an average particle size less than 5 microns; and
   (b) 10 to 60% by weight of at least one water-soluble ammonium or volatile amine salt selected from the group consisting of a salt of a water-insoluble maleinate resin, a salt of a water-insoluble polymer containing maleic acid units and a salt of a water-insoluble polymer containing maleic acid derivative units;

said process for making comprising the step of exposing a mixture of said active substance and at least one water-insoluble compound selected from the group consisting of a maleinate resin, a polymer containing maleic acid units and a polymer containing maleic acid derivative units to the vapors of ammonia or volatile amines to convert said water-insoluble compound into said water-soluble ammonium or volatile amine salt of the compound.

2. The process of claim 1, further including the step of removing any liquid residues.

3. The process of claim 1, wherein said active substances are water-insoluble dyestuffs, dyestuff intermediary products, pigments or optical brighteners.

4. The process of claim 1, wherein said preparation further includes dispersants, wetting agents or diluents.

5. The process of claim 4, wherein said diluents are water-soluble amides or hydroxyl- or ether-compounds present in solid form.

6. The process of claim 1, wherein said preparation contains up to 10% by weight of an anionic or nonionic dispersant or mixtures thereof.

7. The process of claim 1, wherein said preparation contains 50 to 80% by weight of the active substance having an average particle size less than 2 microns and 20 to 50% by weight of the water-soluble salt.

* * * * *